United States Patent [19]

Beck et al.

[11] Patent Number: 4,863,721
[45] Date of Patent: Sep. 5, 1989

[54] REDUCED STINGING ANTIPERSPIRANT COMPOSITIONS

[75] Inventors: Terri A. Beck, Cincinnati; Raymond E. Bolich, Jr., Maineville, both of Ohio

[73] Assignee: The Procter & Gamble Company, Cincinnati, Ohio

[21] Appl. No.: 53,227

[22] Filed: May 22, 1987

[51] Int. Cl.$^4$ .......................... A61K 7/34; A61K 7/36; A61K 7/38; A61K 9/12

[52] U.S. Cl. .............................. 424/47; 424/DIG. 5; 424/66; 424/67; 424/68

[58] Field of Search ..................... 424/DIG. 5, 68, 65, 424/47

[56] References Cited

U.S. PATENT DOCUMENTS

| | | | |
|---|---|---|---|
| 3,018,223 | 1/1962 | Siegal | 424/68 |
| 3,198,708 | 8/1965 | Henkin et al. | 424/68 |
| 3,934,004 | 1/1976 | Orren | 424/68 |
| 3,939,260 | 2/1976 | Lafon | 424/28 |
| 4,036,788 | 7/1977 | Steckler | 260/2.1 E |
| 4,058,491 | 11/1977 | Steckler | 260/2.2 R |
| 4,089,942 | 5/1978 | Bore et al. | 424/47 |
| 4,120,948 | 10/1978 | Shelton | 424/66 |
| 4,126,679 | 11/1978 | Davy et al. | 424/66 |
| 4,152,416 | 5/1979 | Spitzer et al. | 424/46 |
| 4,202,879 | 5/1980 | Shelton | 424/66 |
| 4,383,988 | 5/1983 | Teng et al. | 424/68 |
| 4,425,321 | 1/1984 | Jacquet et al. | 424/47 |

FOREIGN PATENT DOCUMENTS

| | | | |
|---|---|---|---|
| 154465 | 9/1985 | European Pat. Off. | 424/65 |
| 54-157833 | 12/1979 | Japan | 424/47 |
| 54-157834 | 12/1979 | Japan | 424/65 |
| 54-157835 | 12/1979 | Japan | 424/65 |
| 55-4355 | 1/1980 | Japan | 424/65 |
| 1482756 | 8/1977 | United Kingdom | 424/47 |
| 1485373 | 9/1977 | United Kingdom | 424/66 |
| 1501862 | 2/1978 | United Kingdom | 424/68 |
| 2172891 | 10/1986 | United Kingdom | 424/66 |

OTHER PUBLICATIONS

Cosmetics and Toiletries, 12/1985, pp. 27 to 33 and 35 to 41, vol. 100.
Deodorant & Antiperspirant Formulary Cosmetics & Toiletries, 12/1985, vol. 100, pp. 65 to 75.

*Primary Examiner*—Dale R. Ore
*Attorney, Agent, or Firm*—Kim W. Zerby; Steven J. Goldstein; Richard C. Witte

[57] ABSTRACT

Polar solvent-free antiperspirant compositions comprising particulate cellulose ether polymers, preferably hydroxyethyl-cellulose. These antiperspirant compositions produce less stinging and burning than compositions not containing particulate cellulose ether polymers when applied to underarm skin following shaving.

18 Claims, No Drawings

REDUCED STINGING ANTIPERSPIRANT COMPOSITIONS

BACKGROUND OF THE INVENTION

The present invention relates to polar solvent-free antiperspirant compositions which comprise a particulate cellulose ether polymer (preferably a non-ionic cellulose ether polymer); an antiperspirant active; and an anhydrous antiperspirant carrier. These polar solvent-free antiperspirant compositions produce very little burning and stinging when applied to human skin immediately after shaving. The present invention also relates to methods for treating or preventing perspiration and malodor associated with human underarm perspiration.

The use of polymeric materials as gelling agents and/or thickening agents in aqueous antiperspirant compositions is known. For example, the U.S. Pat. No. 4,383,988, to Teng et al, issued May 17, 1983 (incorporated by reference herein in its entirety) discloses aqueous alcoholic gelled antiperspirant compositions containing polymeric carbohydrate derivatives (e.g., hydroxypropyl cellulose acetate) as the gelling agent. This patent further discloses the optional inclusions of thickeners such as methyl cellulose or hydroxyethylcellulose. Other patents disclosing the use of polymers (such as cellulose polymers) in aqueous antiperspirant compositions are: U.S. Pat. No. 3,018,223, to Siegal, issued Jan. 23, 1962; U.S. Pat. No. 3,198,708, to Henkin et al, issued Aug. 3, 1965; and U.S. Pat. No. 3,934,004, to Orren, issued Jan. 20, 1976; the disclosures of all these patents being incorporated herein by reference in their entirety. Cellulose derivatives such as hydroxyalkylcelluloses have also been disclosed as optional components in gel phases containing monohydric alcohols (e.g., ethanol) to help retard alcohol evaporation and to act as an anti-syneresis agent. This use is disclosed in U.S. Pat. No. 4,120,948, to Shelton, issued Oct. 17, 1978 and U.S. Pat. No. 4,202,879, to Shelton, issued May 13, 1980 (the disclosures of both these patents being incorporated herein by reference in their entirety) which patents teach multi-phase antiperspirant sticks having a waxy antiperspirant-containing phase and a gel phase. Finally, U.S. Pat. No. 4,126,679 to Davy, issued Nov. 21, 1978, teaches the use of powdered antiperspirant active salts in solid stick solutions containing certain volatile silicones and long chain alcohols. This patent generally states that optionally the powdered active, which stabilizes the solid solution, may be replaced by any powdered material including talc, sodium bicarbonate, starch, fumed silica and clays.

Notwithstanding this and much more work already performed to develop antiperspirant compositions, the use of antiperspirant compositions immediately after shaving still produces some degree of subjective irritation commonly referred to as "stinging" or "burning". It is an object of the present invention to provide cosmetically-acceptable and efficacious antiperspirant compositions with reduced stinging/burning affects when applied immediately after shaving. It is a further object to provide antiperspirant compositions which are easy to manufacture. Another object of the present invention is to provide methods for treating or preventing perspiration and underarm odor associated with human perspiration.

These and other objects of the present invention will become readily apparent from the detailed description which follows.

All percentages and ratios used herein are by weight unless otherwise specified.

SUMMARY OF THE INVENTION

The present invention relates to polar solvent-free antiperspirant compositions. These compositions comprise:
(a) from about 0.1% to about 10% of at least one particulate cellulose ether polymer;
(b) from about 1% to about 50% of at least one antiperspirant active; and
(c) from about 40% to about 99% of at least one anhydrous antiperspirant carrier.

The present invention also relates to methods for treating or preventing perspiration and malodor associated with human underarm perspiration. These methods comprise applying the to the underarm of a human a safe and effective amount of an antiperspirant composition of the present invention.

DETAILED DESCRIPTION OF THE INVENTION

Polar Solvent-Free Antiperspirant Compositions:

The polar solvent-free antiperspirant compositions of the present invention comprise the following essential components: (a) particulate cellulose ether polymer; (b) antiperspirant active; and (c) anhydrous antiperspirant carrier. In order to obtain the sting reduction benefit from the compositions of the present invention and to avoid solubilizing the particulate cellulose ether polymers, the compositions herein contain in total less than about 2.5%, more preferably less than about 1%, and most preferably essentially 0% of polar solvents. The term "polar solvent", as used herein, means any polar liquid solvent (especially water and mono- or polyhydric alcohols) with a boiling point less than 225° C. This includes water and alcohols such as ethanol, isopropanol, and propylene glycol. As described more fully hereinafter, chemically bound water is not to be considered when determining the water content of the compositions.

The specific components to be included in the antiperspirant compositions of the present invention, and their levels, are selected in order to produce an antiperspirant composition in the desired form, for example, roll-on lotion, aerosol spray, or hard stick. These components, and the weight percentages for these components, are described in detail immediately hereinafter.

(a) Particulate Cellulose Ether Polymers:

The polar solvent-free antiperspirant compositions of the present invention essentially comprise at least one particulate cellulose ether polymer. Preferably, the polymer is selected from non-ionic cellulose ether polymers. More preferred are cellulose ether polymers selected from alkylcelluloses (e.g., methylcellulose), hydroxyalkylalkylcelluloses (e.g., hydroxypropylmethylcellulose; hydroxybutylmethylcellulose; hydroxyethylmethylcellulose; ethylhydroxyethylcellulose), hydroxyalkylcelluloses (e.g., hydroxyethylcellulose; hydroxypropylcellulose), and mixtures thereof. Most preferred are hydroxyalkylcelluloses, especially hydroxyethylcellulose. The cellulose ether polymers typically have molecular weights within the range of from about 20,000 to about 5,000,000, and more typically within the range of from about 50,000 to about 500,000. Cellulose ether polymers are described in "Handbook of Water-Soluble gums and Resins" (McGraw-Hill Book Co., N.Y.; 1980; Davidson, editor), Chapters 3, 4, 12 and 13, the disclosures of which are incorporated herein by reference in their entirety.

The cellulose ether polymers to be utilized herein dissolve in or are miscible with polar solvents such as water and ethanol. However, as utilized in the antiperspirant compositions herein, these polymers are exposed to very little if any polar solvents. Furthermore, the cellulose ether polymers utilized herein are not dissolved in the antiperspirant composition but rather are distributed throughout the composition in particulate form. It is preferred that the particle size be small to prevent the antiperspirant composition from having a "gritty" feel. Preferably, the particle size is less than about 500 microns, more preferably less than about 100 microns, and most preferably about 75 microns or less (especially when used in aerosol spray compositions). In the case of non-spherical particles, the longest dimension of the particles is considered for these preferred limits.

Representative examples of preferred cellulose ether polymers useful in the compositions of the present invention are: hydroxyethylcellulose (Natrosol 250M sold by Hercules Chemical Co.); hydroxypropylcellulose (Klucel sold by Hercules Chemical Co.); and methyl cellulose (Methocel-A supplied by Dow Chemical Co.). Most preferred is hydroxyethylcellulose.

The cellulose ether polymers in total typically comprise from about 0.1% to about 10% by weight of the compositions of the present invention, more preferably from about 0.25% to about 5%, and most preferably from about 1% to about 3%.

(b) Antiperspirant Actives:

The polar solvent-free antiperspirant compositions of the present invention further essentially comprise at least one antiperspirant active. Antiperspirant actives useful in the present invention are well known in the art, and are disclosed generally in Miller and Hoag, "Personal Care Products", *Handbook of Nonprescription Drugs*, 8th Edition, Chapter 19, pages 397–417 (American Pharmaceutical Association; 1986), the disclosures of which are incorporated herein by reference in their entirety. Antiperspirant actives useful herein are also more specifically disclosed in European Patent Application Publication No. 28,853, published May 20, 1981, by Beckmeyer et al.; and European Patent Application Publication No. 117,070, published Aug. 29, 1984, by May, the disclosures of both these patent specifications being incorporated herein by reference in their entirety. Antiperspirant actives include, for example, aluminum chlorohydrates, aluminum chloride, sodium aluminum chlorohydroxy lactate, buffered aluminum sulfate, and aluminum zirconium chlorohydrates.

Preferred are astringent metallic salts including the inorganic and organic salts of aluminum, zirconium and zinc, and mixtures thereof. Particularly preferred are the aluminum and zirconium salts, such as aluminum halides, aluminum hydroxyhalides, zirconyl oxyhalides, zirconyl hydroxyhalides, and mixtures thereof. Such metal salts, and complexes thereof, are described in European Patent Specification Publication No. 117,070, to May, published Aug. 29, 1984, and U.S. Pat. No. 4,137,306, to Rubino et al., issued Jan. 30, 1979, the disclosures of both these patent specifications being incorporated herein by reference in their entirety.

Preferred aluminum salts include those of the formula:

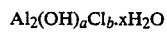

$$Al_2(OH)_aCl_b \cdot xH_2O$$

wherein a is from about 2 to about 5; a+b=6; x is from about 1 to about 6; and wherein a, b, and x may have non-integer values. Particularly preferred are aluminum chlorhydroxides referred to as "5/6 basic chlorhydroxide", wherein a=5; and "⅔ basic chlorhydroxide", wherein a=4. Processes for preparing aluminum salts are disclosed in the following documents, all incorporated by reference herein in their entirety: U.S. Pat. No. 3,887,692, to Gilman, issued June 3, 1975; U.S. Pat. No. 3,904,741, to Jones et al., issued Sept. 9, 1975; U.S. Pat. No. 4,359,456, to Gosling Et al., issued Nov. 16, 1982; and British Patent Specification No. 2,048,229, to Fitzgerald et al., published December 10, 1980. Mixtures of aluminum salts are described in British Patent Specification No. 1,347,950, to Shin et al., published Feb. 27, 1974, the disclosures of which are incorporated herein by reference in their entirety.

Zirconium salts are also preferred for use in antiperspirant compositions of the present invention. Such salts are of the general formula:

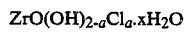

$$ZrO(OH)_{2-a}Cl_a \cdot xH_2O$$

wherein a is from about 1 to about 2, preferably from about 1.5 to about 1.87; x is from about 1 to about 7; and wherein a and x may have non-integer values. These zirconium salts are disclosed in Belgium Patent Specification 825,146, to Achmitz, issued Aug. 4, 1975, the disclosures of which are incorporated herein by reference in their entirety. Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in the following patent documents, all incorporated by reference herein in their entirety: U.S. Pat. No. 2,814,585 to Daley, issued Nov. 26, 1957; U.S. Pat. No. 3,679,068, to Luedders et al., issued Feb. 12, 1974; U.S. Pat. No. 4,017,599, to Rubino, issued Apr. 12, 1977; U.S. Pat. No. 4,120,948, to Shelton, issued Oct. 17, 1978; and British Patent Specification No. 2,144,992, to Callaghan et al., published Mar. 20, 1985.

As is recognized by one skilled in the art, polar solvent-free antiperspirant compositions comprise some amount of water chemically bound as hydrates to the antiperspirant active. This amount of water bound to the antiperspirant active is not detrimental to the ability of the particulate cellulose ether polymer to reduce stinging and burning, and thus this chemically bound water is ignored for purposes of the present invention.

The antiperspirant actives in total typically comprise from about 1% to about 50% by weight of the composition of the present invention, more preferably from about 5% to about 40%, and most preferably from about 5% to about 30%. In addition, it is preferred that the ratio of antiperspirant active to cellulose ether polymer be greater than about 5:1, and more preferably greater than about 10:1.

(c) Anhydrous Antiperspirant Carrier:

The antiperspirant compositions of the present invention also essentially comprise at least one anhydrous antiperspirant carrier. The term "anhydrous", as used herein, means that the carrier materials used in the compositions of the present invention are substantially free of water and other polar solvents (as described hereinbefore) to the extent that the cellulose ether polymer is not dissolved and remains essentially in particulate form. It is preferred that the polar solvents present in the antiperspirant carrier in total be less than about 5%, more preferably less than about 2%, and most preferably essentially 0%.

The selection of anhydrous antiperspirant carriers for use in the compositions of the present invention is readily made of one skilled in the art based on the form of the composition being prepared, for example, aerosol spray, roll-on lotion, or hard stick. Anhydrous antiperspirant carriers are described in detail in European Patent Application Publication No. 28,853, published May 20, 1981, by Beckmeyer et al.; and European Patent Application Publication No. 117,070, published Aug. 29, 1984, by May; the disclosures of both these patent specifications being incorporated herein by reference in their entirety. Carrier materials suitable for use for various composition forms are also described in detail as follows:

(i) Stick Antiperspirant Carriers

The antiperspirant compositions of this invention in stick form preferably contain a volatile polyorganosiloxane, which may function as a liquid emollient. (As used herein, "volatile" refers to those materials which have a measurable vapor pressure at ambient conditions.) The volatile polyorganosiloxanes useful herein may be cyclic or linear. A description of various volatile silcones is found in Todd, et al., "Volatile Silicone Fluids for Cosmetics", 91 *Cosmetics and Toiletries* 27–32 (1976), incorporated by reference herein. Preferred cyclic silicones include polydimethylsiloxanes containing from about 3 to about 9 silicon atoms. Preferred linear silicon oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 345, and Dow Corning 200 (manufactured by the Dow Corning Corporation); Silicone 7207 and Silicon 7158 (manufactured by the Union Carbide Corporation); SF1202 (manufactured by General Electric); and SWS-03314 (manufactured by Stouffer Chemical).

The present antiperspirant compositions in stick form also preferably contain one or more non-volatile emollients. Such materials include fatty acid and fatty alcohol esters, waterinsoluble ethers and alcohols, polyorganosiloxanes, and mixtures thereof. Emollients among those useful herein are described in 1 *Cosmetics, Science and Technology* 27–104 (M. Balsam and E. Saragin ed. 1972), and U.S. Pat. No. 4,202,879, to Shelton, issued May 13, 1980 (both incorporated by reference herein).

The present compositions in stick form preferably contain a non-volatile silicone oil as an emollient material. Such silicon oils include polyalkylsiloxanes, polyalkyarylsiloxanes, and polyethersiloxane copolymers. The essentially non-volatile polyalkyl siloxanes useful herein include, for example polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxane shaving viscosities of from about 15 to about 54 centistokes at 25° C. These are available, for example, as SF 1705 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

The antiperspirant compositions of the present invention in stick form further preferably contain one or more materials having wax-like characteristics and having a melting point from about 65° C. to about 102° C. Such waxes include beeswax, spermaceti, carnauba, baysberry, candelilla, montan, ozokerite, ceresin, paraffin, hydrogenated caster oil (castor wax), synthetic waxes such as Fisher-Tropsch waxes, microcrystalline wax, and mixtures thereof. Caster wax is a preferred high-melting point wax useful herein. Such high-melting point waxes among those useful herein are disclosed in U.S. Pat. No. 4,049,792, to Elsnau, issued Sept. 20, 1977 (incorporated by reference herein).

The present antiperspirant compositions in stick form also preferably contain wax-like materials having a low melting point, i.e., having a melting point of from about 37° C. to about 75° C. Such materials include fatty acids, fatty alcohols, fatty acid esters and fatty acid amides, having fatty chains of from about 8 to about 30 carbon atoms, preferably from about 12 to about 18 carbon atoms, and mixtures thereof. Preferred low melting point waxes include cetyl alcohol, palmitic acid, myristyl alcohol, stearyl alcohol, paraffin, and mixtures thereof. Stearyl alcohol, cetyl alcohol, and mixtures thereof are particularly preferred.

The present antiperspirant sticks preferably contain a finely divided silica material, herein a "colloidal silica material", which is comprised of micron to sub-micron sized silica particulates, with high surface areas (preferably greater than about 100 square meters per gram of material). Preferably, the colloidal silica material is less than about 1 micron in size. Also preferably, the silica material used in the present compositions is a fumed silica. Fumed silicas can generally be described as fluffy, white, superfine powders of extremely low bulk density but having high surface areas. These fumed silicas are typically made by a vapor phase process that produces colloidal silica by the hydrolysis of silicon tetrachloride at a very high temperature. These materials typically consist of about 99.8% silicon dioxide by weight (on a moisture free basis), existing in three dimensional branched chain aggregates, with a surface that is hydrophilic and capable of hydrogen bonding. Such silicas have surface areas ranging from about 2.5 to about 1,200 square meters per gram. Colloidal silica materials are described in Hardy, et al., "The Use of Fumed Silica in Cosmetics", 2 *Cosmetic Technology* 35 (1980), and R. Iler, *The Chemistry of Silica* (1979) (both incorporated by reference herein).

Colloidal silica materials among those useful herein are available from a variety of sources, including Syloid silicas (manufactured by Davison Chemical Division of W. R. Grace), Cab-O-Sil (manufactured by Cabot Corporation), and Aerosil (manufactured by Degussa A.G.). Cab-O-Sil is a particularly preferred commercially available colloidal silica useful herein, with a surface area ranging from about 200 to about 400 square meters per gram.

The antiperspirant sticks of this invention also preferably contain an "inert spherical particulate material" comprising essentially-spherical particulates having a mean diameter of at least about 10 microns. Preferably, the inert spherical particulate material is essentially free of (i.e., containing less than 2% by weight of material) particulates having diameters greater than about 150 microns. Also preferably, the particles have a mean diameter of from about 15 microns to about 75 microns. Commercially-available inert particulate materials among those useful herein may be of a non-uniform size distribution, containing some particles outside the size ranges described herein. For the purposes of this invention, such non-uniform materials preferably have a mean diameter within the ranges described above.

As referred to herein, "inert particulates" are those particulates comprised of materials or mixtures of materials that are essentially water insoluble and which neither melt nor decompose nor react with the wax materials, silicone oils or other components of the antiperspirant sticks, under the conditions of preparation and of use. Among such inert particulate materials that may be incorporated in this invention include those comprised of polyolefins (such as polystyrene, polyethylene, and polypropylene), nylon, Teflon ®, insoluble cross-linked starches, and mixtures thereof.

Preferred inert particulate materials include those comprised of polyolefins, particularly polyethylene. Polyethylene materials, as well as inert particulates made from other polyolefins, can be prepared by any of several methods known in the art. (See, e.g., U.S. Pat. No. 2,825,721, to Hogan, et al., issued Mar. 4, 1958 incorporated by reference herein in its entirety). Polyethylene polymers with low molecular weights of 1,500 to 3,000, as well as polymers of such high molecular weights as 35,000 to 100,000, may be used. One such polyethylene powder useful in this invention is Microthene ®, manufactured by U.S.I. Chemicals, having a mean particle diameter of from about 14 to about 20 microns. Among other commercially-available materials useful herein are 3M Glass Bubbles (soda-lime borosilicate glass spheres sold by 3M Company) and Miralite (low density polyvinylidene chloride hollow microspheres, of approximately 30 microns mean diameter, sold by Pierce & Stevens Chemical Corporation).

In addition to the inert spherical particulate material and the colloidal silica material, the antiperspirant compositions of this invention in stick form preferably contain talc or a talc-like material, herein a "talcum material", which is an inert, soft, impalpable powder. Talc is described in K. S. Plotkin, "Cosmetic Talc" 11 C.T.F.A. Cosmetic Journal 13–16 (1979), incorporated by reference herein. Among talcum materials useful herein are silicate powders (including talc, aluminum silicate, and magnesium silicate), modified corn starches, metallic stearates, and mixtures thereof. Such commercially-available materials include Veecote (anhydrous aluminum silicate, sold by R. T. Vanderbilt Company, Inc.) and Dry Flow (aluminum starch succinate, sold by National Starch and Chemicals Company.

Preferably, the antiperspirant compositions of the present invention in stick form comprise:

(a) from about 35% to about 60% of a volatile silicone oil;
(b) from about 1% to about 5% of a non-volatile emollient;
(c) from about 5% to about 20% of a wax-like material;
(d) from about 15% to about 50% of an antiperspirant active; and
(e) from about 0.1% to about 10% of a particulate cellulose ether polymer.

Preferably, the present antiperspirant sticks contain from about 45% to about 55% of the volatile silicone oils, The non-volatile emollients are preferably present at a level of from about 2.0% to about 4.0%, more preferably from about 2.5% to about 3.5%. The high melting point wax is preferably present at a level of from about 2.5% to about 3.5%, and the low melting point wax preferably present at level of from about 10.5% to about 13%. Preferably, the colloidal silica material is present at a level of from about 0.4% to about 1.0%, more preferably from about 0.4% to about 0.8%. The inert spherical particulate material is preferably present at a level of from about 0.5% to about 1.5%. The talcum material is preferably present at a level of from about 2.5 to about 5.5%, more preferably from about 3% to about 5%. The antiperspirant material is preferably incorporated at a level of from about 15% to about 40%, more preferably from about 20% to about 40%. Preferably, the total level of the inert spherical particulate material and the talcum material is less than about 7%, more preferably less than about 6%. Also, as noted hereinbefore the present compositions are polar solvent-free, preferably containing less than about 2.5% of polar solvents.

The antiperspirant compositions of this invention that are to be made in stick form may be produced using methods among those known in the art. Such processes include those generally comprising the steps of:

(a) admixing the essential and optional composition materials at a temperature sufficient to melt the waxes and dissolve them in the silicone materials;
(b) pouring the composition into stick-form molds, and
(c) cooling to form a solid stick composition.

Typically, the wax materials and silicone materials are admixed at a temperature of from about 70° C. to about 95° C. (depending upon type and level of waxes and other composition components). The bulk composition is typically cooled to a temperature of from about 55° C. to about 60° C. prior to pouring into stick-form molds.

Care should be taken in the processes of making these compositions so as to maintain uniform distribution of particulate materials throughout the antiperspirant sticks. Specific essential and non-essential materials to be included, and their levels, are selected in order to produce a stick of desired hardness, so as to maintain dimensional stability while depositing a suitable amount of antiperspirant material on the skin during normal use. Hardness of sticks can be determined by a variety of methods, including American Society for Testing and Materials (ATM) Method D-5. This method involves the use of a needle of particular weight and dimensions, which is allowed to travel downward through the stick material for a pre-determined period of time. The distance traveled by the needle is a relative measure of the stick hardness. Utilizing Method D-5, with a #1554 penetration needle (manufactured by Sergeant-Welch Scientific Company) weighing 50 grams, and a Precision Model 73515 Penetrometer (manufactured by Precision Scientific, subsidiary of GCA Corporation), the antiperspirant sticks of the present invention preferably yield a penetration of from about 60 to about 150 millimeters, more preferably from about 70 to about 130 millimeters over a period of 5 seconds.

It has been found that, in the processes for making antiperspirant sticks described above, if the temperature of the composition is carefully controlled prior to pouring the composition into stick-form molds, then preferred compositions of this invention may be produced. Such preferred sticks have a matrix comprised of small, randomly-oriented crystals, with few wax crystals in dendritic form. The preferred sticks of this invention thus have an essentially-uniform appearance and color, contrasted in sticks having a readily-visible axial pattern of dendritic wax crystals. In particular, in preferred processes for making the antiperspirant sticks of this invention, the compositions are cooled, immediately prior to step (c) of the process described above, to a temperature at or slightly above the temperature at which the stick composition begins to solidify, but sufficiently high so as to allow pouring of the composition into stick-form molds. In an open batch process, this point in the process is preceded by a significant increase in composition viscosity, and the batch is poured at a temperature less than about 2° C. above the temperature at which the composition fully solidifies. This preferred temperature may vary according to the particular composition employed, and can be easily determined experimentally.

(ii) Aerosol Spray Antiperspirant Carriers

The present compositions in aerosol spray form preferably contain one or more volatile materials, herein "Aerosol propellants", which in a gaseous state, carry the other components of the spray composition in particulate or droplet form. The aerosol propellants useful in the present invention typically have a boiling point within the range of from about −45° C. to about 5° C. The aerosol propellants are liquified when packaged in conventional aerosol containers under pressure. The rapid boiling of the aerosol propellant upon leaving the aerosol containers aids in the atomization of the other components of the present invention.

Aerosol propellants useful in the compositions of the present invention in spray form include those well known in the art. Such aerosol propellants include the chemically-inert hydrocarbons such as propane, n-butane, isobutane and cyclopropane, and mixtures thereof, as well as halogenated hydrocarbons such as dichlorodifluoromethane (propellant 12), 1,1-dichloro-1,1,2,2-tetrafluorethane (propellant 114), 1-chloro-1,1-difluoro-2,2-trifluoroethane (propellant 115), 1-chloro-1,1-difluoroethylene (propellant 142B), 1,1-difluoroethane (propellant 152A), and monochlorodifluoromethane, and mixtures thereof. Isobutane, used singly or admixed with other hydrocarbons, is preferred for use in the present aerosol spray antiperspirants.

The aerosol antiperspirants of the present invention further preferably contain one or more derivatized polydimethyl siloxanes, herein referred to as "functionalized siloxanes", wherein said siloxanes contain electronegative functional groups. Functionalized siloxanes, among those useful herein, include those of the following formula:

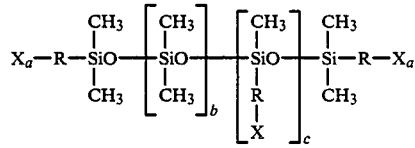

wherein a is 0 or 1, b is from about 50 to about 2000, and c is from about 0 to about 300; X is Cl, F, —COOH, or —N($R^3$)$_2$; R is $CH_3$ (if a=0) or $R^1$ (if a=1); $R^1$ is straight or branched alkyl containing from 1 to 10 carbon atoms; $R^2$ is H or $R^1$; $R^3$ is $R^2$ or $R^1$N($R^2$)$_2$; and wherein a+c is greater than 0 and the ratio of (a+c)/(b+c) is from about 0.01 to about 0.30. It is understood that, in the above formula, the substituted "c" siloxane units may be interspersed with the unsubstituted "b" siloxane units. In preferred functionalized siloxanes of the above formula, b is from about 200 to about 1200, c is from about 2 to about 200, and the ratio of (a+c)/(b+c) is from about 0.01 to about 0.15. Particularly preferred functionalized siloxanes are diamine substituted, wherein X is N$R^2$($R^1$N($R^2$)$_2$).

Molecular weights of preferred functionalized siloxanes useful herein, as determined by gel permeation chromatography/low angle laser light scattering (GPC/LALLS), are from about 2,000 to about 150,000, preferably from about 50,000 to about 150,000. For preferred amino-functional silicones, the ratio (a+c)/(b+c) of the above formula, manifested as milliequivalents of amine per gram (meq/g) of silicone polymer, preferably is from about 0.01 to about 1.5 meq/g, more preferably from about 0.01 to about 0.7 meq.g.

Among the amino-functional silicones useful herein are the following commercially-available materials: Q2-8075 and X2-8107, manufactured by Dow Corning Corporation; Y-7717 and Y-12035, manufactured by Union Carbide Corporation; 756, 784, and 801, manufactured by SWS Silicones Corporation; GE 176-10977 and GE 179-10979, manufactured by General Electric Company; and 2181 manufactured by Petrarch Systems, Inc. Dow Corning Y-12035, GE 176-10977, and SWS 801 are particularly preferred aminofunctional silicone materials useful herein. Among the other commercially-available functionalized (non-amino) siloxanes useful herein are PS402 carboxy-substituted siloxane and PS183 trifluorosubstituted siloxane (manufactured by Petrarch Systems, Inc.).

Another preferred material for use in the present compositions in aerosol spray form is a silicone gum. As referred to herein, "silicone gum" materials useful in the present compositions are those non-functionalized siloxanes having a viscosity of from about 500,000 to about 100,000,000 centistokes at 25° C. These materials are incorporated in the present compositions at a level of from about 0.05% to about 5.0%, preferably from about 0.10% to about 2.0%. Preferred silicone gums include linear and branched polydimethyl siloxanes, of the following general formula:

wherein n is from about 2,000 to about 15,000, preferably from about 2,000 to about 7,000. The silicone gums useful herein may also be substituted with non-electronegative substituents. Silicone gums among those useful herein are available from a variety of commercial sources, including X2-1346 and Dow Corning 200 Fluid (manufactured by Dow Corning Corporation), PS240 (manufactured by Petrarch Systems, Inc.), and SE76, SE30 and SE32 Silicone Gums (manufactured by General Electric Company).

The present compositions also preferably contain an additional solvent material, particularly when the silicone gums described above are also used. Suitable solvents include pentane, hexane, trichlorotrifluoroethylene, trichlorofluoromethane, dichlorofluoromethane, methylene chloride, and volatile and non-volatile non-functionalized silicone oils. Volatile silicone oils (as described hereinbefore) are preferred solvent materials useful in the present aerosol compositions at levels of from about 0.05% to about 15.0%, preferably from about 1.0% to about 5.0%.

The present compositions may also contain a bulking or suspending agent, at levels of from about 0.1% to about 7%, preferably from about 0.4% to about 3.5%. (However, aerosol spray compositions of the present invention typically do not require the presence of a bulking or suspending agent). Such bulking/suspending agents include talc, colloidal silicas, clays and mixtures thereof. Clays and colloidal silicas are particularly preferred. Clay bulking/ suspending agents include montmorillonite clays and hydrophobically treated montmorillonites, e.g., bentonites, hectorites and colloidal magnesium aluminum silicates. These materials are available from a variety of sources, including Laponite hectorite (sold by Laponite Industries, Ltd.) and Veegum magnesium aluminum silicate (sold by R. T. Vanderbilt Co.). A preferred clay bulking/suspending agent is hydrophobically-treated montmorillonite, such as the Bentone bentonites (sold by NL Industries, Inc.). Colloidal silicas are also readily available, such as Cab-O-Sil pyrogenic colloidal silica (sold by Cabot Corporation).

Preferably, the compositions of the present invention in aerosol spray form comprise:
(a) from about 1% to about 40% of an antiperspirant active;
(b) from about 0.1% to about 10% of a particulate cellulose ether polymer; and
(c) from about 50% to about 95% of an aerosol propellant.

Preferably the antiperspirant actives are present at a level of from about 3% to about 24%, more preferably from about 5% to about 12%. Also, preferably, functionalized siloxane is present at a level of from about 0.005% to about 4.0%, more preferably from about 0.005% to about 2.0%, and most preferably from about 0.005% to about 0.1%.

(iii) Roll-on Lotion Antiperspirant Carriers

The antiperspirant compositions of the present invention in roll-on lotion form typically comprise carrier materials similar to those utilized in aerosol spray forms except that no aerosol propellant is required. Antiperspirant compositions in roll-on lotion form, and carrier material useful therein, are described in detail in European Patent Application Publication No. 28,853, published May 20, 1981, by Beckmeyer et al., the disclosures of which are incorporated herein by reference in their entirety.

The compositions of the present invention in any form may also contain optional components which modify the physical characteristics of the vehicles, or serve as "active" components when deposited on the skin in addition to the antiperspirant active. Additional active components include bacteriostats and fungistats. The particular non-active components that may be useful will depend upon the form of application that is desired. Such components include, for example, emollients, colorants, perfumes, and emulsifiers. Optional components useful herein are described in the following documents, all incorporated by reference herein: U.S. Pat. No. 4,049,792, to Elsnau, issued Sept. 20, 1977; Canadian Pat. No. 1,164,347, to Beckmeyer, et al., issued Mar. 27, 1984; European Patent Specification No. 117,070, to May, published Aug. 29, 1984; and Geria, "Formulation of Stick Antiperspirants and Deodorants," 99 Cosmetics & Toiletries 55–60 (1984).

Generally, the anhydrous antiperspirant carriers in total comprise from about 40% to about 99% by weight of the compositions of the present invention, preferably from about 55% to about 95%, and most preferably from about 67% to about 94%.

Methods for Malodor Prevention

The present invention also provides methods for treating or preventing perspiration and malodor associated with human underarm perspiration. These methods comprise applying to the underarm skin of a human a safe and effective amount of an antiperspirant composition of the present invention. The term "a safe and effective amount", as used herein, is an amount which is effective in eliminating or substantially reducing perspiration and the malodor associated with human underarm perspiration while being safe for human use at a reasonable risk/benefit ratio.

The following examples further describe and demonstrate embodiments within the scope of the present invention. The examples are given solely for the purpose of illustration and are not to be construed as limitations of the present invention as many variations thereof are possible without departing from the spirit and scope.

EXAMPLE I

Roll-On Composition Containing Hydroxyethylcellulose

A polar solvent-free antiperspirant composition of the present invention in roll-on form containing hydroxyethylcellulose is prepared comprising the following ingredients:

| Components | Weight % |
|---|---|
| Zirconium-Aluminum-Glycine-Hydroxychloride[1] | 26.70 |
| Cyclomethicone/Dimethicone Blend[2] | 60.66 |
| Polyethylene[3] | 5.50 |
| Quaternium 18 Hectorite[4] | 3.50 |
| Natrosol 250M (75 micron)[5] | 2.00 |
| Propylene Carbonate | 1.60 |
| Magnesium Aluminum Silicate | 0.02 |
| Fragrance | 0.02 |

[1]Supplied by Westwood Chemical Co.
[2]Silicone blend supplied by Dow Corning and General Electric
[3]Supplied by U.S.I. Chemicals
[4]Supplied by N. L. Industries
[5]Hydroxyethylcellulose supplied by Hercules Chemical Co.

This roll-on lotion composition is prepared as follows. To a batch tank is added the cyclomethicone/dimethicone blend, followed by the polyethylene and then the magnesium aluminum silicate, and this mixture is mixed for 10 minutes. The propylene carbonate is added and mixed for 5 minutes, after which time the hydroxyethylcellulose (sifted through a 200 mesh screen; particle size approximately 75 microns) is added and then mixed for 10 minutes. The zirconium-aluminum-glycine-hydroxychloride is added to this mixture and mixed for 10 minutes. Fragrance is added and mixed for a minimum of 5 minutes (the final batch should mix about 15–20 minutes). The batch is milled to about 750 cps (630–930 cps), and then this lotion is added to roll-on bottles.

This antiperspirant composition is applied to the underarm skin of a human to effectively prevent perspiration and underarm odor resulting from perspiration. This composition produces less stinging or burning when applied to freshly shaven underarm skin than compositions which do not contain the particulate hydroxyethylcellulose.

EXAMPLE II

Solid Stock Composition Containing Hydroxyethylcellulose

A polar solvent-free antiperspirant composition of the present invention in solid stick form containing hydroxyethylcellulose is prepared comprising the following ingredients:

| Components | Weight % |
| --- | --- |
| Aluminum-Zirconium-Hydroxychloride-Glycine[1] | 26.70 |
| Cyclomethicone[2] | 47.718 |
| Dimethicone[3] | 3.00 |
| Stearyl Alcohol | 11.35 |
| Talc | 4.75 |
| Hydrogentated Castor Oil[4] | 2.90 |
| Natrosol 250M (75 Micron)[5] | 2.00 |
| Microthene[6] | 1.00 |
| Fumed Silica[7] | 0.50 |
| Eicosanol | 0.052 |
| Fragrance | 0.03 |

[1]Supplied by Westwood Chemical Co.
[2]Supplied by General Electric
[3]Supplied by Dow Corning
[4]Supplied by CAS Chemical
[5]Hydroxyethylcellulose supplied by Hercules Chemical Co.
[6]Supplied by USI Chemical
[7]Cab-O-Sil supplied by Cabot Industries This solid stick composition is prepared as follows using a jacketted batch tank. To this tank is added cyclomethicone and dimethicone which is mixed for 5 minutes as the tank is being heated to 180° F. (81° C.). The fumed silica is added and mixed for 5 minutes, followed by the addition of stearyl alcohol and mixing for 10 minutes or until melted. Castor wax is added and mixed for 10 minutes or until melted. Eicosanol is added followed by the talc, and then mixed for 5 minutes. The Microthene is added next (mixed 5 minutes), followed by the hydroxyethylcellulose (sifted through a 200 mesh screen; particle size approximately 75 microns; mixed 10 minutes). The antiperspirant active is added, mixed for about 10–15 minutes at 180° F. (81° C.), and then the batch tank is cooled to 160°–165° F. (71°–74° C.). To the cooled batch is added fragrance (mixed 5–10 minutes), and then the batch is cooled further to 140°–145° F. (60°–63° C.). At this temperature the liquid is poured into canisters, and allowed to solidify and cool to room temperature.

This antiperspirant composition is applied to the underarm skin of a human to effectively prevent underarm perspiration and odor resulting from perspiration. This composition produces less stinging or burning when applied to freshly shaven underarm skin than stick compositions not containing the particulate hydroxyethylcellulose.

EXAMPLE III

Aerosol Composition Containing Hydroxyethylcellulose

A polar solvent-free antiperspirant composition of the present invention in aerosol spray form containing hydroxyethylcellulose is prepared comprising the following ingredients:

| Components | Weight % |
| --- | --- |
| Impalpable I-ACH[1] | 9.195 |
| Cyclomethicone[2] | 5.300 |
| Dimethicone 350csk[3] | 1.000 |
| Isopropyl Myristate | 2.500 |
| Tixogel VP[4] | 0.280 |
| Bentone 38[5] | 0.080 |
| Propylene Carbonate | 0.090 |
| Fragrance | 0.005 |
| Natrosol 250M (75 micron)[6] | 0.820 |
| A-31 propellent[7] | 80.730 |

[1]Improved activated aluminum chlorohydrate supplied by Westwood Chemical Co.
[2]Cyclomethicone D5 supplied by Dow Corning
[3]Supplied by Dow Corning
[4]Quaternium 18 Bentonite clay supplied by United Catalyst
[5]Quaternium 18 Hectorite clay supplied by N. L. Industries
[6]Hydroxyethylcellulose supplied by Hercules Chemical Co.
[7]Isobutane supplied by Phillips This aerosol spray is prepared as follows. To a batch tank at room temperature is added the cyclomethicone, dimethicone, and isopropyl myristate, and then mixed for 5 minutes. The Bentonite is added next (mixed 5–10 minutes), followed by the propylene carbonate (mixed 5 minutes), followed by the Hectorite (mixed 5 minutes), and then the hydroxyethylcellulose (75 micron particle size; mixed 10 minutes). To this mixture is added the antiperspirant active (mixed 15–20 minutes) and then the fragrance (mixed 5–10 minutes). The batch is milled to about 50,000 cps. This mixture is packaged in aerosol spray cans which are then charged with the propellent.

This antiperspirant composition is applied to the underarm skin of a human to effectively prevent underarm perspiration and odor resulting from perspiration. This composition produces less stinging or burning when applied to freshly shaven underarm skin than compositions not containing particulate hydroxyethylcellulose.

EXAMPLE IV

Solid Stick Composition Containing Methylcellulose

A polar solvent-free antiperspirant composition of the present invention in solid stick form containing methyl cellulose is prepared comprising the following ingredients:

| Components | Weight % |
| --- | --- |
| Aluminum-Zirconium-Chorohydroxy-Glycine[1] | 26.70 |
| Cyclomethicone[2] | 42.00 |
| Stearyl Alcohol | 11.37 |
| Talc | 7.00 |
| PPG-14 Butyl Ether[3] | 5.77 |
| Castor Wax[4] | 5.00 |
| Methylellulose[5] | 2.00 |
| Eicosanol | 0.13 |

-continued

| Components | Weight % |
| --- | --- |
| Pentadecalactone | 0.03 |

[1] Supplied by Reheis
[2] Supplied by Dow Corning
[3] Supplied by Union Carbide
[4] Supplied by CAS Chemical
[5] Methocel-A supplied by Dow Chemical Co.

This solid stick composition is prepared by a procedure similar to that described in Example II.

This antiperspirant composition is applied to the underarm skin of a human to effectively prevent underarm perspiration and odor resulting from perspiration. This composition produces less stinging or burning when applied to freshly shaven underarm skin than compositions not containing particulate methylcellulose.

EXAMPLE V

Roll-on Composition Containing Hydroxyethylmethylcellulose

A polar solvent-free antiperspirant composition of the present invention in roll-on form containing hdyroxyethylmethylcellulose is prepared comprising the following ingredients:

| Components | Weight % |
| --- | --- |
| Zirconium-Aluminum-Glycine-Hydroxychloride[1] | 26.70 |
| Cyclomethicone/Dimethicone Blend[2] | 60.68 |
| Polyethylene | 5.50 |
| Quaternium-18 Hectorite[3] | 3.50 |
| Hydroxyethylmethylcellulose | 2.00 |
| Propylene Carbonate | 1.60 |
| Ethylene Brassylate[4] | 0.02 |

[1] Supplied by Reheis
[2] Supplied by General Electric
[3] Supplied by N. L. Industries
[4] Supplied by Polarome/Emery This roll-on composition is prepared by a procedure similar to that described in Example I.

This antiperspirant composition is applied to the underarm skin of a human to effectively prevent underarm perspiration and odor resulting from perspiration. This composition produces less stinging or burning when applied to freshly shaven underarm skin than compositions not containing particulate hydroxyethylmethylcellulose.

What is claimed is:

1. An antiperspirant composition containing no more than about 1% polar solvents comprising:
   (a) from about 0.1% to about 10% of at least one particulate nonionic cellulose ether polymer selected from the group consisting of methyl cellulose, hydroxyalkylcelluloses, and mixtures thereof;
   (b) from about 1% to about 50% of at least one antiperspirant active; and
   (c) from about 40% to about 99% of at least one anhydrous antiperspirant carrier.

2. An antiperspirant composition according to claim 1 wherein the particulate nonionic cellulose ether polymer is hydroxyethylcellulose.

3. An antiperspirant composition in stick form containing no more than about 1% polar solvents comprising:
   (a) from about 0.1% to about 10% of a particulate nonionic cellulose ether polymer having particle size of less than about 500 microns selected from the group consisting of methyl cellulose, hydroxyalkylcelluloses, and mixtures thereof;
   (b) from about 1% to about 50% of at least one antiperspirant active; and
   (c) from about 40% to about 99% of at least one anhydrous stick antiperspirant carrier.

4. An antiperspirant composition in stick form according to claim 3 comprising:
   (a) from about 35% to about 50% of a volatile silicone oil;
   (b) from about 1% to about 5% of a non-volatile emollient;
   (c) From about 5% to about 20% of a wax-like material;
   (d) from about 15% to about 50% of an antiperspirant active; and
   (e) from about 0.1% to about 10% of a particulate nonionic cellulose ether polymer having particle size of less than about 500 microns selected from the group consisting of methyl cellulose, hydroxyalkylcelluloses, and mixtures thereof.

5. An antiperspirant composition in stick form according to claim 4 wherein the particulate nonionic cellulose ether polymer is hydroxyethylcellulose.

6. An antiperspirant composition in stick form according to claim 5 wherein the hydroxyethylcellulose has particle size of less than about 100 microns.

7. An antiperspirant composition in roll-on lotion form containing no more than about 1% polar solvent comprising:
   (a) from about 0.1% to about 10% of a particulate nonionic cellulose there polymer having particle size of less than about 500 microns selected from the group consisting of methyl cellulose, hydroxyalkylcelluloses, and mixtures thereof;
   (b) from about 1% to about 50% of at least one antiperspirant active; and
   (c) from about 40% to about 99% of at least one anhydrous roll-on lotion carrier.

8. An antiperspirant composition in roll-on lotion form according to claim 7 wherein the particulate nonionic cellulose ether polymer is hydroxyethylcellulose.

9. An antiperspirant composition in roll-on lotion form according to claim 8 wherein the hydroxyethylcellulose has particle size of less than about 100 microns.

10. An antiperspirant composition in aerosol spray form containing no more than about 1% polar solvent comprising:
    (a) from about 0.1% to about 10% of a particulate nonionic cellulose ether polymer having particle size of less than about 10 microns selected from the group consisting of methyl cellulose, hydroxyalkylcelluloses, and mixtures thereof;
    (b) from about 1% to about 50% of at least on antiperspirant active; and
    (c) from about 40% to about 99% of at least one anhydrous aerosol spray carrier.

11. An antiperspirant composition in aerosol spray form according to claim 10 comprising:
    (a) from about 1% to about 40% of an antiperspirant active;
    (b) from about 0.1% to about 10% of a particulate nonionic cellulose ether polymer having particle size of less than about 100 microns selected from the group consisting of methyl cellulose, hydroxyalkylcelluloses, and mixtures thereof; and
    (c) from about 60% to about 95% of an aerosol propellant.

12. An antiperspirant composition in aerosol spray form according to claim 11 wherein the particulate nonionic cellulose ether polymer is hydroxyethylcellulose.

13. An antiperspirant composition in aerosol spray form according to claim 12 wherein the hydroxyethylcellulose has particle size of 75 microns or less.

14. A method for treating or preventing malodor associated with human underarm perspiration, said methods comprising applying to the underarm skin of a human a safe and effective amount of an antiperspirant composition according to claim 1.

15. A method for treating or preventing malodor associated with human underarm perspiration, said methods comprising applying to the underarm skin of a human a safe and effective amount of an antiperspirant composition according to claim 2.

16. A method for treating or preventing malodor associated with human underarm perspiration, said methods comprising applying to the underarm skin of a human a safe and effective amount of an antiperspirant composition according to claim 6.

17. A method for treating or preventing malodor associated with human underarm perspiration, said methods comprising applying to the underarm skin of a human a safe and effective amount of an antiperspirant composition according to claim 9.

18. A method for treating or preventing malodor associated with human underarm perspiration, said methods comprising applying to the underarm skin of a human a safe and effective amount of an antiperspirant composition according to claim 13.

* * * * *

UNITED STATES PATENT AND TRADEMARK OFFICE
CERTIFICATE OF CORRECTION

PATENT NO. : 4,863,721

DATED : September 5, 1989

INVENTOR(S) : Terri A. Beck and Raymond E. Bolich, Jr.

It is certified that error appears in the above-identified patent and that said Letters Patent is hereby corrected as shown below:

Column 6, line 5, "siloxane shaving" should be -- siloxanes having --.

Column 6, line 6, "15 to about 54" should be -- 15 to about 65 --.

Column 10, line 29, "preferably from about 50,000" should be -- preferably from about 20,000 --, and after "150,000" the following should be inserted -- more preferably from about 50,000 to about 150,000. --

Column 11, line 16, "5.0%" should be -- 6.0% --.

Column 11, line 43 "50%" should be -- 60% --.

Column 16, line 9 in Claim 4, "50%" should be -- 60% --.

Column 16, line 51 in Claim 10, "10 microns" should be -- 100 microns --.

Signed and Sealed this

Twentieth Day of August, 1991

*Attest:*

HARRY F. MANBECK, JR.

*Attesting Officer*  *Commissioner of Patents and Trademarks*